United States Patent
Nishioka et al.

(10) Patent No.: US 7,759,483 B2
(45) Date of Patent: Jul. 20, 2010

(54) 3-ALKENYLCEPHEM COMPOUNDS AND PROCESS FOR PRODUCTION THEREOF

(75) Inventors: Yoichi Nishioka, Tokushima (JP); Koichi Sorajo, Tokushima (JP); Yutaka Kameyama, Tokushima (JP)

(73) Assignee: Otsuka Chemical Co., Ltd., Osaka (JP)

( * ) Notice: Subject to any disclaimer, the term of this patent is extended or adjusted under 35 U.S.C. 154(b) by 704 days.

(21) Appl. No.: 11/628,247

(22) PCT Filed: Jun. 2, 2005

(86) PCT No.: PCT/JP2005/010531

§ 371 (c)(1), (2), (4) Date: Dec. 1, 2006

(87) PCT Pub. No.: WO2005/118596

PCT Pub. Date: Dec. 15, 2005

(65) Prior Publication Data

US 2008/0064869 A1 Mar. 13, 2008

(30) Foreign Application Priority Data

Jun. 4, 2004 (JP) ............................. 2004-166726

(51) Int. Cl.
*C07D 501/12* (2006.01)
*C07D 501/24* (2006.01)
(52) U.S. Cl. ...................... 540/220; 540/226
(58) Field of Classification Search ................. 540/226, 540/220
See application file for complete search history.

(56) References Cited

U.S. PATENT DOCUMENTS

| | | | |
|---|---|---|---|
| 4,839,350 A | 6/1989 | Atsumi et al. | 514/202 |
| 5,616,703 A | 4/1997 | Ludescher et al. | 540/226 |
| 6,235,897 B1 * | 5/2001 | Ludescher et al. | 540/226 |
| 6,288,223 B1 | 9/2001 | Okada et al. | 540/220 |
| 7,459,550 B2 * | 12/2008 | Prabhat et al. | 540/227 |
| 2006/0173175 A1 * | 8/2006 | Prabhat et al. | 540/222 |
| 2008/0033166 A1 * | 2/2008 | Nishioka et al. | 540/226 |

FOREIGN PATENT DOCUMENTS

| | | |
|---|---|---|
| JP | 7-188250 A | 7/1995 |
| JP | 2002-234893 A | 8/2002 |
| WO | 2005/016936 A2 | 2/2005 |

\* cited by examiner

*Primary Examiner*—Mark L Berch
(74) *Attorney, Agent, or Firm*—Kubovcik & Kubovcik

(57) ABSTRACT

A 3-alkenylcephem compound of the formula (1)

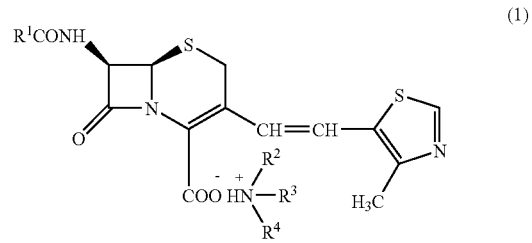

wherein $R^1$ is benzyl or phenoxymethyl, $R^2$, $R^3$ and $R^4$ are alike or different and are each a hydrogen atom, $C_{1-10}$ alkyl, $C_{4-8}$ cycloalkyl or aryl $C_{1-3}$ alkyl substituted or unsubstituted with $C_{1-4}$ alkyl, $R^2$ and $R^3$, when taken together, form a group —$(CH_2)_l X_m (CH_2)_n$— substituted or unsubstituted with $C_{1-4}$ alkyl at an optional position, X is an oxygen atom or group —$N(R^5)$—, l is 0 to 3, m is 0 or 1, n is an integer of 2 to 4, $R^5$ is a hydrogen atom or $C_{1-4}$ alkyl.

13 Claims, No Drawings

3-ALKENYLCEPHEM COMPOUNDS AND PROCESS FOR PRODUCTION THEREOF

This application is a 371 of international application PCT/JP2005/010531 filed Jun. 2, 2005, which claims priority based on Japanese patent application No. 2004-166726 filed Jun. 4, 2004, which is incorporated herein by reference.

TECHNICAL FIELD

The present invention relates to novel amine salts of 7-substituted acylamino-3-[2-(4-methylthiazol-5-yl)vinyl]-3-cephem-4-carboxylic acid and to a process for preparing the same. The invention relates also to a process for preparing 7-amido-3-[2-(4-methylthiazol-5-yl)vinyl]-3-cephem-4-carboxylic acid and amine salts thereof which are improved in the content of 7-substituted acylamino-3-[(Z)-2-(4-methylthiazol-5-yl)vinyl]-3-cephem-4-carboxylic acid or the amine salt thereof.

BACKGROUND ART

An oral cephem agent, cefditoren pivoxil of the formula (4), is in wide used as an antibacterial agent having a broad antimicrobial spectrum and strong antibacterial activities.

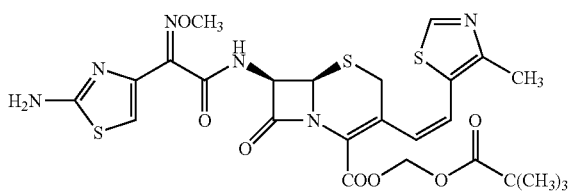

(4)

With cephalosporin antibiotics having alkenyl at the 3-position, the steric structure of the alkenyl group at the 3-position has Z configuration as is the case with cefditoren pivoxil. The mechanism of producing outstanding antibacterial activities on gram-negative bacteria is attributable partly to this feature. For the antibacterial pharmaceutical agent to exhibit its effect, therefore, it is important to diminish to the greatest possible extent the presence of the geometrical E-isomer of cefditoren pivoxil. In preparing cefditoren pivoxil, attempts have been made to improve the Z-isomer content of process intermediates.

For example, a process has been disclosed for preparing an amine salt of Z/E mixture of 7-amino-3-[2-(4-methylthiazol-5-yl)vinyl]-3-cephem-4-carboxylic acid, a process intermediate and depleting the amine salt of 7-amino-3-[(E)-2-(4-methylthiazol-5-yl)vinyl]-3-cephem-4-carboxylic acid by crystallization (see, for example, Patent Literature 1).

[Patent Literature 1] JP1995-188250 A

The process disclosed in the literature, however, is not satisfactory in the yields of the desired 7-amino-3-[2-(4-methylthiazol-5-yl)vinyl]-3-cephem-4-carboxylic acid and the salt thereof which are depleted in the E-isomer content, and the amine salt can not be filtered off efficiently. Thus, the process can not be said to be a suitable process from an economical viewpoint (see Comparative Example 1).

An object of the present invention is to provide a 3-alkenylcephem compound useful as an intermediate in the process for preparing cefditoren pivoxil which is in wide use as an excellent antibacterial agent.

Another object of the invention is to provide an economically outstanding and industrially suitable process for preparing a 3-alkenylcephem compound which is improved in Z-isomer content.

DISCLOSURE OF THE INVENTION

1. A 3-alkenylcephem compound of the formula (1)

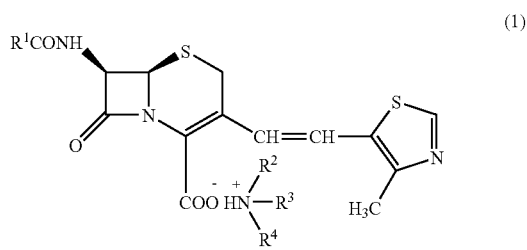

(1)

wherein $R^1$ is benzyl or phenoxymethyl, $R^2$, $R^3$ and $R^4$ are alike or different and are each a hydrogen atom, $C_{1-10}$ alkyl, $C_{4-8}$ cycloalkyl or aryl $C_{1-3}$ alkyl substituted or unsubstituted with $C_{1-4}$ alkyl, $R^2$ and $R^3$, when taken together, form a group $-(CH_2)_l X_m (CH_2)_n-$ substituted or unsubstituted with $C_{1-4}$ alkyl at an optional position, X is an oxygen atom or group $-N(R^5)-$, l is 0 to 3, m is 0 or 1, n is an integer of 2 to 4, $R^5$ is a hydrogen atom or $C_{1-4}$ alkyl.

2. A 3-(Z)-alkenylcephem compound of the formula (1a)

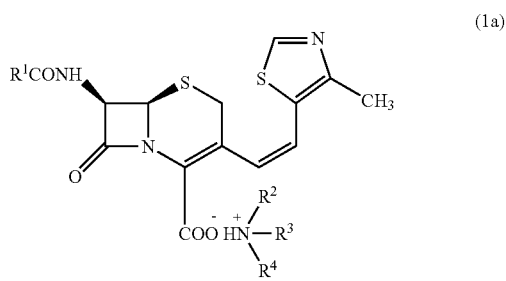

(1a)

wherein $R^1$, $R^2$, $R^3$ and $R^4$ are the same as above.

3. A process for preparing a 3-alkenylcephem compound of the formula (1) characterized by reacting an amine compound of the formula (3) with a 3-alkenylcephem compound of the formula (2)

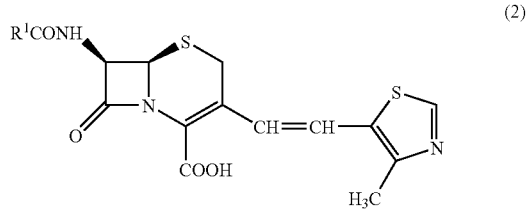

(2)

wherein $R^1$ is the same as above

(3)

wherein $R^2$, $R^3$ and $R^4$ are the same as above.

4. A process for preparing a 3-alkenylcephem compound of the formula (2) which is improved in the content of a 3-(Z)-alkenylcephem compound of the formula (2a), the process being characterized by adding at least one of organic solvents including alcohols, ethers, aliphatic hydrocarbons, alicyclic ketones and aliphatic ketones to a solution of a 3-alkenylcephem compound of the formula (1) in water or in a solvent mixture of water and at least one organic solvent selected from among alcohols, aliphatic ketones, esters, amides and nitrites for crystallization to obtain a solution or suspension of a 3-alkenylcephem compound of the formula (1) which is improved in the content of a 3-(Z)-alkenylcephem compound of the formula (1a), and adjusting the solution or suspension to a pH of 0.5 to 4

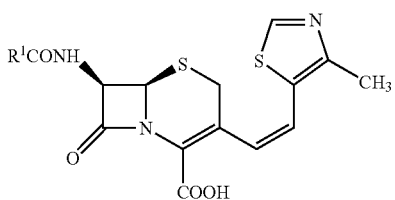

(2a)

wherein $R^1$ is the same as above.

5. A process for preparing a 3-alkenylcephem compound of the formula (1) which is improved in the content of a 3-(Z)-alkenylcephem compound of the formula (1a), the process being characterized by adding at least one of organic solvents including alcohols, ethers, aliphatic hydrocarbons, alicyclic ketones and aliphatic ketones to a solution of a 3-alkenylcephem compound of the formula (1) in water or in a solvent mixture of water and at least one organic solvent selected from among alcohols, aliphatic ketones, esters, amides and nitrites to crystallize the 3-alkenylcephem compound of the formula (1).

6. A process for preparing a 3-alkenylcephem compound of the formula (2) which is improved in the content of a 3-(Z)-alkenylcephem compound of the formula (2a), the process being characterized by adjusting a solution or suspension of a 3-alkenylcephem compound of the formula (1) which is improved in the content of a 3-(Z)-alkenylcephem compound of the formula (1a) to a pH of 0.5 to 4.

The present invention further includes the following embodiments.

7. A 3-alkenylcephem compound according to par. 1 or 2 which is in the form of an amine salt of a 3-alkenylcephem compound of the formula (1) or (1a), the amine salt being a tert-butylamine salt, tert-octylamine salt, dicyclohexylamine salt, benzylamine salt or N-methylpiperazine salt.

8. A 3-alkenylcephem compound according to pars. 1 and 7 which contains at least 96% of a 3-(Z)-alkenylcephem compound of the formula (1a).

9. A process for preparing a 3-alkenylcephem compound of the formula (1) characterized by reacting an amine compound of the formula (3) with a 3-alkenylcephem compound of the formula (2) containing up to 20% of a 3-(E)-alkenylcephem compound of the formula (2b)

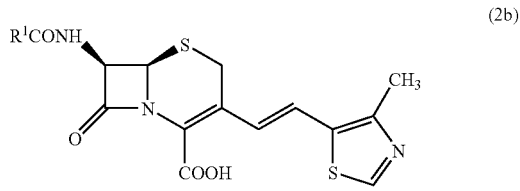

(2b)

wherein $R^1$ is the same as defined above.

10. A process for preparing a 3-alkenylcephem compound according to pars. 3 and 9 characterized in that the amine compound of the formula (3) is reacted in an amount of 1.0 to 2.0 moles with the 3-alkenylcephem compound of the formula (2) per mole thereof.

11. A process for preparing a 3-alkenylcephem compound according to pars. 3 and 9 characterized in that the amine compound of the formula (3) is reacted in an amount of 1.0 to 1.5 moles with the 3-alkenylcephem compound of the formula (2) per mole thereof.

12. A process for preparing a 3-alkenylcephem compound according to pars. 3, 9, 10 and 11 wherein the amine compound of the formula (3) is tert-butylamine, tert-octylamine, dicyclohexylamine, benzylamine or N-methylpiperazine.

13. A process according to par. 5 for preparing a 3-alkenylcephem compound of the formula (1) which is improved in the content of a 3-(Z)-alkenylcephem compound of the formula (1a), the process being characterized by adding at least one of organic solvents including alcohols, ethers, aliphatic hydrocarbons, alicyclic ketones and aliphatic ketones to a solution of a 3-alkenylcephem compound of the formula (1) containing up to 20% of a 3-(E)-alkenylcephem compound of the formula (1b) in water or in a solvent mixture of water and at least one organic solvent selected from among alcohols, aliphatic ketones, esters, amides and nitrites to crystallize the 3-alkenylcephem compound of the formula (1)

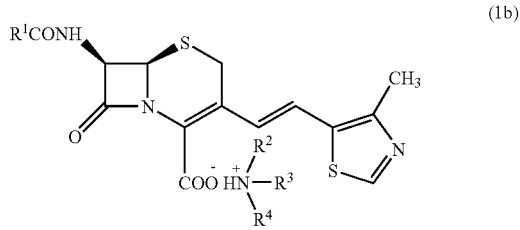

(1b)

wherein $R^1$, $R^2$, $R^3$ and $R^4$ are the same as above.

14. A process according to par. 5 or 13 for preparing a 3-alkenylcephem compound of the formula (1) which is improved in the content of a 3-(Z)-alkenylcephem compound of the formula (1a), the process being characterized by adding 3 to 30 parts by volume of at least one of organic solvents including alcohols, ethers, aliphatic hydrocarbons, alicyclic ketones and aliphatic ketones to a solution of 1 part by weight of a 3-alkenylcephem compound of the formula (1) in 2 to 50 parts by volume of water or a solvent mixture of water and at least one organic solvent selected from among alcohols, aliphatic ketones, esters, amides and nitrites for crystallization.

15. A process according to pars. 5, 13 and 14 for preparing a 3-alkenylcephem compound of the formula (1) improved in the content of a 3-(Z)-alkenylcephem compound of the formula (1a) wherein the solvent mixture of water and organic solvent is an acetone/water solvent mixture or methanol/water solvent mixture.

16. A process according to pars. 5, 13, 14 and 15 for preparing a 3-alkenylcephem compound of the formula (1) improved in the content of a 3-(Z)-alkenylcephem compound of the formula (1a) wherein the solvent mixture of water and organic solvent has a mixing ratio of 1 to 10 parts by volume of the organic solvent per part by volume of water.

17. A process according to pars. 5, 13 and 14 for preparing a 3-alkenylcephem compound of the formula (1) improved in the content of a 3-(Z)-alkenylcephem compound of the formula (1a) wherein the organic solvent to be added to the solution of the 3-alkenylcephem compound of the formula (1) is methanol, diethyl ether, diisopropyl ether, acetone, n-hexane or n-hexanone.

18. A process according to pars. 5 and 13 to 17 for preparing a 3-alkenylcephem compound of the formula (1) improved in the content of a 3-(Z)-alkenylcephem compound of the formula (1a) wherein the content of the 3-(Z)-alkenylcephem compound of the formula (1a) is at least 96%.

19. A process for preparing a 3-(Z)-alkenylcephem compound of the formula (2a) according to par. 6, the process being characterized by dissolving or suspending a 3-(Z)-alkenylcephem compound of the formula (1a) in water and adjusting the resulting solution or suspension to a pH of 0.5 to 4 with a mineral acid.

20. A process for preparing a 3-alkenylcephem compound of the formula (2) which is improved in the content of a 3-(Z)-alkenylcephem compound of the formula (2a), the process being characterized by dissolving or suspending a 3-alkenylcephem compound of the formula (1) which is improved in the content of a 3-(Z)-alkenylcephem compound of the formula (1a) in water and adjusting the resulting solution or suspension to a pH of 0.5 to 4 with a mineral acid.

21. A process according to pars. 6, 19 and 20 for preparing a 3-alkenylcephem compound of the formula (2) improved in the content of a 3-(Z)-alkenylcephem compound of the formula (2a) wherein the content of the 3-(Z)-alkenylcephem compound of the formula (2a) is at least 96%.

In an attempt to fulfill the above objects, we have conducted intensive research and found out a novel amine salt of 4-position carboxylic acid compound which has an amide structure at the 7-position on a cephem ring. Surprisingly, the use of the amine salt compound remarkably improves the yield of the 3-alkenylcephem compound to be prepared and improved in Z-isomer content. The present invention has been accomplished based on this finding.

Examples of the groups herein represented by $R^2$, $R^3$ and $R^4$ are given below.

Examples of $C_{1-4}$ alkyl groups are straight-chain or branched-chain alkyl groups having 1 to 4 carbon atoms, such as methyl, ethyl, n-propyl, isopropyl, n-butyl, sec-butyl and tert-butyl.

Examples of $C_{1-10}$ alkyl groups are straight-chain or branched-chain alkyl groups having 1 to 10 carbon atoms, such as n-pentyl, isopentyl, neopentyl, n-hexyl, isohexyl, n-heptyl, n-octyl, tert-octyl (=2,4,4-trimethylpent-2-yl), n-nonyl and n-decyl, in addition to the substituents of $C_{1-4}$ alkyl groups mentioned.

Examples of $C_{4-8}$ cycloalkyl groups are cycloalkyl groups having 4 to 8 carbon atoms, such as cyclobutyl, cyclopentyl, cyclohexyl, cycloheptyl and cyclooctyl.

Examples of aryl $C_{1-3}$ alkyl groups are straight-chain or branched-chain alkyl groups having 1 to 3 carbon atoms and substituted with an aryl group having 6 to 10 carbon atoms, such as benzyl, phenethyl, 1-phenylethyl, 1-phenylpropyl and naphthylmethyl. Such groups may have 1 to 3 $C_{1-4}$ alkyl groups at an optional position on an aryl group.

Examples of groups —$(CH_2)_l X_m (CH_2)_n$— are bivalent saturated hydrocarbon groups having 3 to 6 carbon atoms, such as trimethylene group, tetramethylene group, pentamethylene group and hexamethylene group, the group —NH—$(CH_2)_3$—, group —$CH_2$—NH—$(CH_2)_2$—, group —$(CH_2)_2$—NH—$(CH_2)_2$—, group —$CH(CH_3)CH_2$—NH—$(CH_2)_2$—, group —$(CH_2)_2$—N(CH_3)—$(CH_2)_2$—, group —$CH_2$—O—$(CH_2)_2$—, group —$(CH_2)_2$—O—$(CH_2)_2$—, etc. Such groups may have a $C_{1-4}$ alkyl group at an optional position.

In the 3-alkenylcephem compound of the formula (1) and the 3-(Z)-alkenylcephem compound of the formula (1a), $R^2$, $R^3$ and $R^4$ are alike or different and are each preferably a hydrogen atom, methyl, ethyl, n-butyl, tert-butyl, 2-ethyl-1-hexyl, tert-octyl, cyclopentyl, cyclohexyl, benzyl, 4-methylbenzyl, phenethyl and 1-phenylethyl; and $R^2$ and $R^3$ preferably form tetramethylene group, pentamethylene group, hexamethylene group, the group —NH—$(CH_2)_3$—, group —$CH_2$—NH—$(CH_2)_2$—, group —$(CH_2)_2$—NH—$(CH_2)_2$—, group —$CH(CH_3)CH_2$—NH—$(CH_2)_2$—, group —$(CH_2)_2$—N(CH_3)—$(CH_2)_2$—, group —$CH_2$—O—$(CH_2)_2$— and group —$(CH_2)_2$—O—$(CH_2)_2$—.

Described in greater detail, examples of preferred amine salts of the 3-alkenylcephem compound of the formula (1) are ammonium salt, ethylamine salt, diethylamine salt, triethylamine salt, n-butylamine salt, tert-butylamine salt, 2-ethyl-1-hexylamine salt, tert-octylamine salt, cyclopentylamine salt, dicyclopentylamine salt, cyclohexylamine salt, dicyclohexylamine salt, benzylamine salt, 4-methylbenzylamine salt, dibenzylamine salt, (R)-phenethylamine salt, 1-phenylethylamine salt, pyrrolidine salt, imidazolidine salt, piperidine salt, piperazine salt, 2-methylpiperazine salt, N-methylpiperazine salt, morpholine salt, N-methylmorpholine salt, oxazolidine salt, etc. More preferable among these are tert-butylamine salt, tert-octylamine salt, dicyclohexylamine salt, benzylamine salt and N-methylpiperazine salt.

The 3-alkenylcephem compound of the formula (1) of the present invention is easily prepared by the process of the following reaction scheme-1.

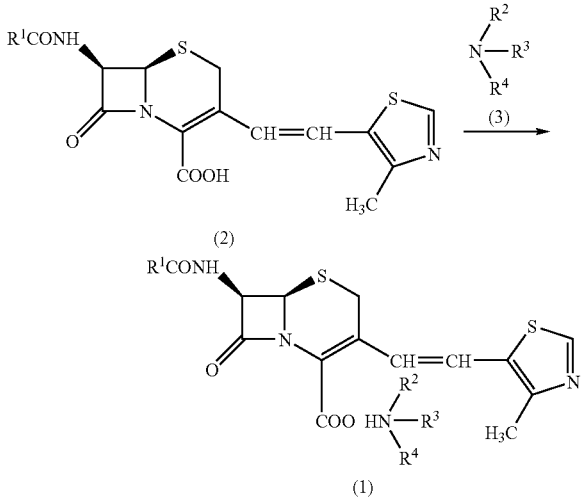

wherein $R^1$, $R^2$, $R^3$ and $R^4$ are the same as above.

According to the above reaction scheme, the 3-alkenyl-cephem compound of the formula (1) is prepared by reacting an amine compound of the formula (3) with a 3-alkenyl-cephem compound of the formula (2) in a suitable solvent.

Although the solvent to be used differs depending on the amine compound to be used and the amine salt to be prepared, the solvent is, for example, water, or a solvent mixture of water and an organic solvent. Examples of useful organic solvents are methanol, ethanol, isopropyl alcohol, n-propyl alcohol, n-butyl alcohol, isobutyl alcohol and like alcohols, acetone, methyl ethyl ketone, methyl isobutyl ketone and like ketones, ethyl acetate, isopropyl acetate, butyl acetate and like esters, N,N-dimethylformamide and like amides, acetonitrile and like nitriles, etc. Especially preferable among such solvents are an acetone/water solvent mixture and methanol/water solvent mixture.

The mixing ratio of the organic solvent to water is 1 to 10 parts by volume, preferably 1.5 to 8 parts by volume, more preferably 2 to 5 parts by volume, of the organic solvent per part by volume of water.

The solvent is used in an amount sufficient to dissolve or suspend the 3-alkenylcephem compound of the formula (2) therein although the amount differs with the kind of solvent to be used. The solvent is used, for example, in an amount of about 2 to about 50 parts by volume, preferably about 3 to about 40 parts by volume, most preferably about 5 to about 25 parts by volume, per part by weight of the 3-alkenylcephem compound of the formula (2).

The 3-alkenylcephem compound of the formula (2) to be used in the present reaction can be prepared by known processes. The compound can be prepared by synthesizing a 3-[2-(4-methylthiazol-5-yl)vinyl]-3-cephem-4-carboxylic acid ester and effecting a deprotecting reaction for the 4-position carboxylic acid protective group thereof, for example, by the processes disclosed in The Journal of Antiobiotics, Vol. XLIII, No. 8, 1047-1050 (1990), Chem. Pharm. Bull. 39(9), 2433-2436 (1991), JP1987-19593A, JP1991-64503B, Journal of Synthetic Organic Chemistry, Japan, Vol. 60, No. 2, 155-161 (2002), etc. Usable for the deprotecting reaction are various procedures generally known for the deprotecting reaction of the carboxylic acid ester protective group of β-lactam compounds. Useful are, for example, a method of catalytic reduction with use of a noble metal, and acid treatment methods disclosed in Am. Chem. Soc. 91, 5674 (1969), Chem. Pharm. Bull. 30, 4545 (1982), Tetrahedron Lett. 2793 (1979), JP1994-4638B, etc.

The 3-alkenylcephem compound of the formula (2) to be used in the present reaction is a 3-(E/Z)-alkenylcephem compound comprising a 3-(Z)-alkenylcephem compound of the formula (2a) and a 3-(E)-alkenylcephem compound of the formula (2b) which are conjointly present. The 3-(E/Z)-alkenylcephem compound contains preferably up to 20%, more preferably about 1 to about 15%, most preferably about 4 to about 12%, of the 3-(E)-alkenylcephem compound of the formula (2b).

With the process of the present invention, it is possible to repeatedly perform the procedure to be described below in order to achieve a further improved Z-isomer content. Accordingly, the 3-(E/Z)-alkenylcephem compound can be used favorably even when up to 4% or 1% in E-isomer content.

The term "E-isomer content" as used herein means the proportion of the E-isomer present in the combined amount of the E-isomer and the Z-isomer. The E-isomer content is given by E-isomer content (%)=100×(amount of E-isomer present)/{(amount of E-isomer present)+(amount of Z-isomer present)}

The amine compounds of the formula (3) for use in the present reaction are preferably those wherein $R^2$, $R^3$ and $R^4$ are alike or different and are each preferably a hydrogen atom, methyl, ethyl, n-butyl, tert-butyl, 2-ethyl-1-hexyl, tert-octyl, cyclopentyl, cyclohexyl, benzyl, 4-methylbenzyl, phenethyl and 1-phenylethyl; and $R^2$ and $R^3$ preferably form tetramethylene group, pentamethylene group, hexamethylene group, the group —NH—$(CH_2)_3$—, group —$CH_2$—NH—$(CH_2)_2$—, group —$(CH_2)_2$—NH—$(CH_2)_2$—, group —CH$(CH_3)CH_2$—NH—$(CH_2)_2$—, group —$(CH_2)_2$—N$(CH_3)$—$(CH_2)_2$—, group —$CH_2$—O—$(CH_2)_2$— and group $(CH_2)_2$—O—$(CH_2)_2$—. More specific examples of preferred amine compounds are ammonium, ethylamine, diethylamine, triethylamine, n-butylamine, tert-butylamine, 2-ethyl-1-hexylamine, tert-octylamine, cyclopentylamine, dicyclopentylamine, cyclohexylamine, dicyclohexylamine, benzylamine, 4-methylbenzylamine, dibenzylamine, (R)-phenethylamine, 1-phenylethylamine, pyrrolidine, imidazolidine, piperidine, piperazine, 2-methylpiperazine, N-methylpiperazine, morpholine, N-methylmorpholine, oxazolidine, etc. More preferable among these are tert-butylamine, tert-octylamine, dicyclohexylamine, benzylamine and N-methylpiperazine. These amine compounds are usable singly, or at least two of them can be used in combination.

The amine compound is used in an amount of 1.0 to 2.5 moles, preferably 1.0 to 2.0 moles, more preferably 1.0 to 1.5 moles, per mole of the 3-alkenylcephem compound of the formula (2).

The reaction temperature, which varies with the amine to be used and the amine salt to be obtained, is up to 10° C., preferably about 0 to about 5° C. The reaction time is such that the reaction is conducted until the compound of the formula (2) serving as the starting material disappears. The reaction is completed generally in 0.5 to 7 hours.

The 3-alkenylcephem compound of the formula (1) to be prepared by the present reaction is a 3-(E/Z)-alkenylcephem compound retaining the E/Z isomer content ratio of the 3-alkenylcephem compound of the formula (2) used.

The solution (reaction mixture) of the 3-alkenylcephem compound of the formula (1) resulting from the present reaction is usable as it is for the process for preparing the 3-alkenylcephem compound of the formula (1) to be described below and improved in the content of 3-alkenylcephem compound of the formula (1a).

The 3-alkenylcephem compound of the formula (1) which is improved in the content of 3-alkenylcephem compound of the formula (1a) can be produced by preparing a solution of the 3-alkenylcephem compound of the formula (1) comprising an E-isomer and a Z-isomer which are conjointly present and adding an organic solvent to the solution.

The preferred solvent to be used is one which is capable of adjusting the solubility product. It is important that the Z-isomer (1a) of the compound of the formula (1) and the E-isomer (1b) thereof be different in solubility in the solvent. The greater the difference between the solubilities, the more suitable the solvent is to the process of the invention. Examples of suitable solvents are methanol, ethanol, isopropyl alcohol and like alcohols, diethyl ether, diisopropyl ether, tetrahydrofuran, 1,4-dioxane and like ethers, n-hexane, n-heptane, n-octane, cyclohexane, cycloheptane, cyclooctane and like aliphatic hydrocarbons, cyclohexanone, cycloheptanone, cyclooctanone and like alicyclic ketones, acetone, methyl ethyl ketone, methyl isobutyl ketone and like aliphatic ketones, etc.

Preferable among these are methanol, diethyl ether, diisopropyl ether, n-hexane, n-hexanone and acetone.

These solvents are used, for example, in an amount of about 3 to 30 parts by volume, preferably about 4 to about 25 parts by volume, most preferably about 5 to about 20 parts by volume, per part by weight of 3-alkenylcephem compound of the formula (1).

The solubility product adjusting solvent is added to the solution of the 3-alkenylcephem compound of the formula (1), whereby a 3-(Z)-alkenylcephem compound of the formula (1a) is crystallized generally selectively.

It is desired to effect the crystallization at a low temperature of 0 to 10° C., preferably of 0 to not higher than 5° C.

The crystals separating out are collected by a usual method such as filtration, whereby a 3-alkenylcephem compound of the formula (1) can be obtained which is improved in the content of 3-(Z)-alkenylcephem compound of the formula (1a).

The content of the 3-(Z)-alkenylcephem compound of the formula (1a) in the 3-alkenylcephem compound of the formula (1) obtained by the process of the invention varies with the content of the 3-(E)-alkenylcephem compound of the formula (2b) in the 3-alkenylcephem compound of the formula (2) used. If the content of the 3-(E)-alkenylcephem compound of the formula (2b) is up to 20%, the 3-alkenylcephem compound of the formula (1) usually contains at least 96%, preferably 97 to 99.99%, more preferably 99 to 99.95%, of the 3-(Z)-alkenylcephem compound of the formula (1a). The process of the invention can be repeated in order to achieve a further improved content.

The 3-alkenylcephem compound of the formula (1) obtained by the process of the invention and improved in the content of the 3-(Z)-alkenylcephem compound of the formula (1a) is dissolved or suspended in water, and a mineral acid, such as hydrochloric acid, sulfuric acid or phosphoric acid, is thereafter added to the solution or suspension to adjust the pH thereof to an acidity of 0.5 to 4, whereby a 3-alkenylcephem compound of the formula (2) can be prepared which is improved in the content of 3-(Z)-alkenylcephem compound of the formula (2a).

The amount of water to be used is not limited-particularly but may be such that the 3-alkenylcephem compound of the formula (1) can be fully dissolved or suspended therein. For example, about 5 to about 50 parts by volume of water is used per part by weight of the 3-alkenylcephem compound of the formula (1).

The 3-alkenylcephem compound of the formula (2) is crystallized by adjusting the pH, and the crystals separated out are filtered off, washed with water and dried, whereby a 3-alkenylcephem compound of the formula (2) can be obtained which is improved in the content of 3-(Z)-alkenylcephem compound of the formula (2a).

It is likely that crystals fail to separate out depending, for example, on the kind of amine salt and the amount of water. In this case, the product can be crystallized by subjecting the aqueous solution to extraction with at least one of organic solvents such as methyl ethyl ketone, methyl isobutyl ketone and like ketones, ethyl acetate, butyl acetate and like esters, methylene chloride, chloroform and like hydrocarbon halides, and benzene, toluene and like aromatic hydrocarbons, concentrating the organic solvent in a vacuum for a volume reduction, and thereafter adding a poor solvent comprising methanol, ethanol, isopropyl alcohol and like lower alcohol, and diethyl ether, diisopropyl ether and like lower ether.

The process of the invention, when repeated, further reduces the E-isomer content of 3-alkenylcephem compound of the formula (2).

BEST MODE OF CARRYING OUT THE INVENTION

The present invention will be described below in detail with reference to Reference Examples, Examples and Comparative Example. However, the invention is in no way limited to Examples.

Incidentally, 3-alkenylcephem compounds of the formula (1) will be referred to as compounds (1), and 3-alkenylcephem compounds of the formula (2) as compounds (2).

The E-isomer contents and the Z-isomer contents in Reference Examples, Examples and Comparative Examples were each calculated from the foregoing equation using the corresponding area value obtained by HPLC as the amount of the isomer present. The measurement conditions are as follows.

a) HPLC Measurement Conditions 1

Column [YMC-AM312 (ODS) 6.0 diam×150 mm], column temp. (constant temp. around 25° C.), mobile phase (acetonitrile/buffer=50/50, buffer: prepared by dissolving 7.29 g of $NaH_2PO_4.2H_2O$ and 0.464 g of $Na_2HPO_4$ in 1 liter of distilled water), flow rate (1.0 ml/min.), detecting wavelength (274 nm), injection (10 μl), scanning time: 45 min., Z-isomer retention time (16-17 min.), E-isomer retention time (21-22 min.).

b) HPLC Measurement Conditions 2

Column [YMC-AM312 (ODS) 6.0 diam×150 mm], column temp. (constant temp. around 25° C.), mobile phase (acetonitrile/buffer=50/75, buffer: prepared by dissolving 7.8 g of $NaH_2PO_4.2H_2O$ in 1 liter of distilled water), flow rate (1.0 ml/min.), detecting wavelength (254 nm), injection (10 μl), scanning time: 30 min., Z-isomer retention time (10-11 min.), E-isomer retention time (12-13 min.).

REFERENCE EXAMPLE 1

A 10.0 g quantity of 7-phenylacetamido-3-[2-(4-methylthiazol-5-yl)vinyl]-3-cephem-4-carboxylic acid diphenylmethyl ester (E-isomer content: 10.0% by HPLC[a]) prepared according to the method disclosed in Journal of Synthetic Oraganic Chemistry, Japan. Vol. 60, No. 2, 155-161 (2002) was measured out and placed into a four-necked 500-ml flask, and 55 ml of phenol was added to the ester, followed by stirring at 50 to 55° C. for 5 hours. To the reaction mixture were added 100 ml of ethyl acetate and 200 ml of 5% aqueous solution of sodium hydrogencarbonate, and the mixture was then cooled to not higher than 10° C. The organic layer was removed, and the aqueous layer was collected and washed with 150 ml of ethyl acetate three times. To the aqueous solution were added 100 ml of ethyl acetate and 3 ml of 2N hydrochloric acid, the mixture was stirred, the organic layer was collected and concentrated in a vacuum, and 200 ml of diethyl ether was thereafter added to the concentrate for crystallization. The crystals were filtered off, washed with 200 ml of diethyl ether and dried, affording 7.20 g of a compound (2) ($R^1$=benzyl, E-isomer: 10.0% by HPLC[b]).

$^1$H-NMR (DMSO-$d_6$, ppm from TMS): 2.36 (3H, s, $CH_3$), 3.32 (1H, d, S—CH(H), 19.5 Hz), 3.50 (1H, d, S—CH(H), 19.5 Hz), 3.53 (2H, ABq, $CH_2$—(Ph), 9.3 Hz, 15.0 Hz), 5.16

(1H, d, S—CH, 4.8 Hz), 5.70 (1H, dd, N—CH, 7.5 Hz, 4.8 Hz), 6.34 (1H, d, =CH—, 12.0 Hz), 6.71 (1H, d, =CH—Ar, 12.0 Hz), 7.2-7.3 (5H, m, Ph), 8.94 (1H, s, S—CH=N), 9.14 (1H, d, NH, 8.1 Hz)

REFERENCE EXAMPLE 2

A 10.0 g quantity of 7-phenoxyacetamido-3-[2-(4-methylthiazol-5-yl)vinyl]-3-cephem-4-carboxylic acid p-methoxybenzyl ester (E-isomer content: 9.0% by HPLC[a)]) prepared according to the method disclosed in Journal of Synthetic Oraganic Chemistry, Japan. Vol. 60, No. 2, 155-161 (2002) was measured out and placed into a four-necked 500-ml flask, and 60 ml of cresol was added to the ester, followed by stirring at 45 to 50° C. for 6 hours. To the reaction mixture were added 100 ml of methyl isobutyl ketone and 200 ml of 5% aqueous solution of sodium hydrogencarbonate, and the mixture was then cooled to not higher than 10° C. The organic layer was removed, and the aqueous layer was collected and washed with 150 ml of methyl isobutyl ketone three times. To the aqueous solution were added 100 ml of methyl isobutyl ketone and 3 ml of 2N hydrochloric acid, the mixture was stirred, the organic layer was collected and concentrated in a vacuum, and 200 ml of diisopropyl ether was thereafter added to the concentrate for crystallization. The crystals were filtered off, washed with 200 ml of diisopropyl ether and dried, affording 7.60 g of a compound (2) ($R^1$=phenoxymethyl, E-isomer: 9.0% by HPLC[b)]).

$^1$H-NMR (DMSO-$d_6$, ppm from TMS): 2.36 (3H, s, $CH_3$), 3.32 (1H, d, S—CH(H), 19.5 Hz), 3.50 (1H, d, S—CH(H), 19.5 Hz), 4.92 (2H, ABq, $CH_2$—(Ph), 9.3 Hz, 15.0 Hz), 5.16 (1H, d, S—CH, 4.8 Hz), 5.70 (1H, dd, N—CH, 7.5 Hz, 4.8 Hz), 6.34 (1H, d, =CH—, 12.0 Hz), 6.71 (1H, d, =CH—Ar, 12.0 Hz), 7.1-7.2 (5H, m, Ph), 8.94 (1H, s, S—CH=N), 9.14 (1H, d, NH, 8.1 Hz)

EXAMPLE 1

[Procedure 1]

A 3.0 g quantity of the compound (2) ($R^1$=benzyl, E-isomer: 10.0% by HPLC[b)]) prepared in Reference Example 1 was added to and dissolved in a solvent mixture of 8.5 ml of water and 21.5 ml of acetone in a four-necked 100-ml flask. The solution was cooled to not higher than 5° C., 1.1 g of tert-octylamine was added to the solution, and the mixture was stirred for 3 hours, affording a reaction mixture of compound (1). To the reaction mixture was added 20 ml of acetone, and the crystals separating out were filtered off, washed with water and acetone and dried, giving a compound (1) ($R^1$=benzyl, $R^2$=tert-octyl, $R^3$=$R^4$=hydrogen atom). The filtration time was about 1 minute in all of Examples.

Yield: 3.47 g

Z-isomer yield: 99.3%

E-isomer content: 0.08% (Z-isomer content: 99.92%)

$^1$H-NMR (DMSO-$d_6$, ppm from TMS): 0.94 (9H, s, $C(CH_3)_3$), 1.28 (6H, s, N—C—$(CH_3)_2$), 1.55 (2H, s, N—C—$CH_2$), 2.29 (3H, s, $CH_3$), 2.98 (1H, d, S—CH(H), 17.1 Hz), 3.29 (1H, d, S—CH(H), 17.1 Hz), 3.47, 3.55 (2H, ABq, $CH_2$—(Ph), 13.8 Hz), 5.11 (1H, d, S—CH, 4.5 Hz), 5.51 (1H, dd, N—CH, 8.4 Hz, 4.5 Hz), 6.34 (1H, d, =CH—, 11.7 Hz), 6.67 (1H, d, =CH—Ar, 11.7 Hz), 7.2-7.3 (5H, m, Ph), 8.89 (1H, s, S—CH=N), 9.05 (1H, d, NH, 8.4 Hz)

[Procedure 2]

The compound (1) obtained was suspended in 30 ml of water, and the suspension was adjusted to a pH of 1 with 6N hydrochloric acid and stirred, but no crystals precipitated. The suspension was then subjected to extraction with addition of 30 ml of ethyl acetate, the ethyl acetate was evaporated off in a vacuum, 20 ml of diethyl ether was added to the concentrate, and the resulting crystals were filtered off, washed with diethyl ether and dried, giving a compound (2) ($R^1$=benzyl).

Yield: 2.60 g

Z-isomer yield: 97.1% (procedure 2), 96.4% (procedures 1+2)

E-isomer content: 0.08% (Z-isomer content: 99.92%)

EXAMPLE 2

[Procedure 1]

A 3.0 g quantity of the compound (2) ($R^1$=phenoxymethyl, E-isomer: 9.0% by HPLC[b)]) prepared in Reference Example 2 was added to and dissolved in a solvent mixture of 8.5 ml of water and 21.5 ml of acetone in a four-necked 100-ml flask. The solution was cooled to not higher than 5° C., 0.85 g of benzylamine was added to the solution, and the mixture was stirred for 4 hours, affording a reaction mixture of compound (1). To the reaction mixture was added 21.5 ml of acetone, and the crystals separating out were filtered off, washed with water and acetone and dried, giving a compound (1) ($R^1$=phenoxymethyl, $R^2$=benzyl, $R^3$=$R^4$=hydrogen atom)

Yield: 3.25 g

Z-isomer yield: 96.4%

E-isomer content: 0.10% (Z-isomer content: 99.9%)

$^1$H-NMR (DMSO-$d_6$, ppm from TMS): 2.30 (3H, s, $CH_3$), 3.04 (1H, d, S—CH(H), 17.1 Hz), 3.32 (1H, d, S—CH(H), 17.1 Hz), 3.95 (2H, s, (Ph)—$CH_2$—N), 4.88, 4.95 (2H, ABq, $CH_2$—(Ph), 13.8 Hz), 5.04 (1H, d, S—CH, 4.5 Hz), 5.55 (1H, dd, N—CH, 8.4H, 4.5 Hz), 6.41 (1H, d, =CH—, 11.7 Hz), 6.62 (1H, d, =CH—Ar, 11.7 Hz), 7.1-7.5 (10H, m, Ar), 8.91 (1H, s, S—CH=N), 9.08 (1H, d, NH, 8.4 Hz)

[Procedure 2]

The compound (1) obtained was suspended in 30 ml of water, and the suspension was adjusted to a pH of 2 with 6N hydrochloric acid and stirred, but no crystals precipitated. The suspension was then subjected to extraction with addition of 30 ml of methylene chloride, the methylene chloride was evaporated off in a vacuum, 10 ml of diisopropyl ether was added to the concentrate, and the resulting crystals were filtered off, washed with diisopropyl ether and dried, giving a compound (2) ($R^1$=phenoxymethyl).

Yield: 2.63 g

Z-isomer yield: 100% (procedure 2), 96.4% (procedures 1+2)

E-isomer content: 0.10% (Z-isomer content: 99.9%)

EXAMPLE 3

[Procedure 1]

A 3.0 g quantity of the compound (2) ($R^1$=benzyl, E-isomer: 10.0% by HPLC[b)]) prepared in Reference Example 1 was added to and dissolved in a solvent mixture of 8.5 ml of water and 25 ml of acetone in a four-necked 100-ml flask. The solution was cooled to not higher than 5° C., 1.6 g of dicyclohexylamine was added to the solution, and the mixture was stirred for 2 hours and thereafter stirred at 10° C. for 30 minutes, affording a reaction mixture of compound (1).

To the reaction mixture was added 25 ml of acetone, and the crystals separating out were filtered off, washed with water and acetone and dried, giving a compound (1) ($R^1$=benzyl, $R^2$=$R^3$=cyclohexyl, $R^4$=hydrogen atom)

Yield: 3.77 g

[Procedure 2]

The compound (1) obtained was suspended in 60 ml of water, and the suspension was adjusted to a pH of 3.5 with 6N hydrochloric acid and stirred with ice cooling for 1 hour for aging. The resulting crystals were filtered off, washed with water and diethyl ether and dried, giving a compound (2) ($R^1$=benzyl)

Yield; 2.59 g

Z-isomer yield: 96.8% (procedure 2), 95.7% (procedures 1+2)

E-isomer content: 0.11% (Z-isomer content: 99.89%)

EXAMPLE 4

A 3.0 g quantity of the compound (2) ($R^1$=benzyl, E-isomer: 10.0% by $HPLC^{b)}$) prepared in Reference Example 1 was added to and dissolved in a solvent mixture of 12.5 ml of water and 51.5 ml of acetone in a four-necked 100-ml flask. The solution was cooled to not higher than 5° C., 0.85 g of N-methylpiperazine was added to the solution, and the mixture was stirred for 3 hours, affording a reaction-mixture of compound (1).

To the reaction mixture was added 50 ml of methanol, and the crystals separating out were filtered off, washed with water and methanol and dried, giving a compound (1) ($R^1$=benzyl, $R^2$, $R^3$=the group —$(CH_2)_2$—$N(R^5)(CH_2)_2$—, $R^4$=hydrogen atom, $R^5$=methyl).

Yield: 3.21 g

Z-isomer yield: 96.8%

E-isomer content: 0.09% (Z-isomer content: 99.91%)

$^1$H-NMR (DMSO-$d_6$, ppm from TMS): 2.15 (3H, s, N—$CH_3$), 2.31 (3H, s, $CH_3$), 2.43 (4H, m, piperazine ring), 2.94 (4H, m, piperazine ring), 3.05 (1H, d, S—CH(H), 17.4 Hz), 3.33 (1H, d, S—CH(H), 17.4 Hz), 3.48, 3.55 (2H, ABq, $CH_2$—(Ph), 13.5 Hz), 5.05 (1H, d, S—CH, 4.8 Hz), 5.55 (1H, dd, N—CH, 8.4 Hz, 4.8 Hz), 6.43 (1H, d, =CH—, 11.7 Hz), 6.57 (1H, d, =CH—Ar, 11.7 Hz), 7.2-7.3 (5H, m, Ph), 8.90 (1H, s, S—CH=N), 9.07 (1H, d, NH, 8.4 Hz)

[Procedure 2]

The compound (1) obtained was suspended in 30 ml of water, and the suspension was adjusted to a pH of 0.5 with 6N hydrochloric acid and stirred, but no crystals precipitated. The suspension was then subjected to extraction with addition of 50 ml of chloroform, the chloroform was evaporated off in a vacuum, 15 ml of isopropyl alcohol was added to the concentrate, and the resulting crystals were filtered off, washed with isopropyl alcohol and dried, giving a compound (2) ($R^1$=benzyl).

Yield; 2.53 g

Z-isomer yield: 96.6% (procedure 2), 93.5% (procedures 1+2)

E-isomer content: 0.09% (Z-isomer content: 99.91%)

EXAMPLE 5

[Procedure 1]

A 3.0 g quantity of the compound (2) ($R^1$=benzyl, E-isomer: 10.0% by $HPLC^{b)}$) prepared in Reference Example 1 was added to and dissolved in a solvent mixture of 7.5 ml of water and 22.5 ml of acetone in a four-necked 100-ml flask. The solution was cooled to not higher than 5° C., 0.65 g of tert-butylamine was added to the solution, and the mixture was stirred for 4 hours, affording a reaction mixture of compound (1). To the reaction mixture was added 22.5 ml of acetone, and the crystals separating out were filtered off, washed with water and acetone and dried, giving a compound (1) ($R^1$=benzyl, $R^2$=tert-butyl, $R^3$=$R^4$=hydrogen atom).

Yield: 3.07 g

Yield: 97.4%

E-isomer content: 0.10% (Z-isomer content: 99.9%)

$^1$H-NMR (DMSO-$d_6$, ppm from TMS): 1.34 (9H, s, C($CH_3$)$_3$), 2.29 (3H, s, $CH_3$), 2.98 (1H, d, S—CH(H), 17.1 Hz), 3.29 (1H, d, S—CH(H), 17.1 Hz), 3.47, 3.55 (2H, ABq, $CH_2$—(Ph), 13.8 Hz), 5.11 (1H, d, S—CH, 4.5 Hz), 5.51 (1H, dd, N—CH, 8.4 Hz, 4.5 Hz), 6.34 (1H, d, =CH—, 11.7 Hz), 6.67 (1H, d, =CH—Ar, 11.7 Hz), 7.2-7.3 (5H, m, Ph), 8.89 (1H, s, S—CH=N), 9.05 (1H, d, NH, 8.4 Hz)

[Procedure 2]

The compound (1) obtained was suspended in 30 ml of water, and the suspension was adjusted to a pH of 1 with 6N hydrochloric acid and stirred, but no crystals precipitated. The suspension was then subjected to extraction with addition of 30 ml of ethyl acetate, the ethyl acetate was evaporated off in a vacuum, 20 ml of diethyl ether was added to the concentrate, and the resulting crystals were filtered off, washed with diethyl ether and dried, giving a compound (2) ($R^1$=benzyl)

Yield; 2.54 g

Z-isomer yield: 96.7% (procedure 2), 94.3% (procedures 1+2)

E-isomer content: 0.10% (Z-isomer content: 99.9%)

COMPARATIVE EXAMPLE 1

[Procedure 1]

A 1.0 g quantity of 7-amino-3-[2-(4-methylthiazol-5-yl) vinyl]-3-cephem-4-carboxylic acid (E-isomer: 9% by $HPLC^{b)}$) was suspended in a solvent mixture of 2 ml of water and 5 ml of methanol in a four-necked 100-ml flask. With addition of 0.68 ml of dicyclohexylamine, the suspension was stirred until crystals separated out from a transparent solution subsequently formed. The reaction mixture was allowed to stand at room temperature for 15 minutes and thereafter stirred for 15 minutes, and 7 ml of acetone was then slowly added to the mixture. The resulting mixture was subsequently cooled in an ice bath for 2 hours, and the resulting crystals were filtered off, washed with acetone and dried, affording 7-amino-3-[2-(4-methylthiazol-5-yl)vinyl]-3-cephem-4-carboxylic acid dicyclohexylamine salt. While the filtration treatment in Examples was completed in about 1 minute, the filtration procedure in this comparative example required about 10 minutes.

Yield: 0.81 g

Yield: 57.0%

E-isomer content: 0.12%

$^1$H-NMR ($D_2O$, ppm from TMS): 1.1-2.0 (20H, m, cyclohexyl), 2.39 (3H, s, $CH_3$), 3.2-3.3 (2H, m, cyclohexyl), 3.32 (1H, d, S—CH(H), 18.3 Hz), 3.57 (1H, d, S—CH(H), 18.3 Hz), 4.80 (1H, d, S—CH, 4.9 Hz), 5.21 (1H, d, N—CH, 4.9 Hz), 6.32, 6.64 (2H, ABq, HC=CH—, 11.7 Hz), 8.78 (1H, s, S—CH=N)

[Procedure 2]

The dicyclohexylamine salt compound obtained was suspended in 30 ml of water, the suspension was adjusted to a pH of 3.5 with dilute sulfuric acid and stirred with ice cooling for 30 minutes for aging, and the crystals separating out were filtered off, washed with water and acetone and dried, giving 7-amino-3-[2-(4-methylthiazol-5-yl)vinyl]-3-cephem-4-carboxylic acid.

Yield: 0.37 g

Z-isomer yield: 71.45 (procedure 2), 40.7% (procedures 1+2)

E-isomer-content: 0.12%

REFERENCE EXAMPLE 3

The compounds (2) obtained in Examples 1 to 4 can all be efficiently converted to cefditoren pivoxil. Cefditoren pivoxil can be prepared, for example, from the compound (2) ($R^1$=benzyl) obtained in Example 1 by conducting a hydrolysis reaction at the 7-position by a known technique using penicillin G acylase enzyme in an alkaline aqueous solution, followed by a process disclosed in Japanese Patent No. 2846186 or Journal of Synthetic Organic Chemistry, Japan, Vol. 60, No. 2, 155-161 (2002).

INDUSTRIAL APPLICABILITY

The use of a 3-alkenylcephem compound of the invention makes it possible to easily prepare 7-substituted acylamino-3-[2-(4-methylthiazol-5-yl)vinyl]-3-cephem-4-carboxylic acid having an exceedingly high Z-isomer content from 7-substituted acylacmino-3-[2-(4-methylthiazol-5-yl)vinyl]-3-cephem-4-carboxylic acid comprising an E-isomer and Z-isomer which are conjointly present. The carboxylic acid compound obtained can be used industrially advantageously as an intermediate for producing cefditoren pivoxil which is in wide use as an excellent antibacterial agent.

The invention claimed is:

1. A process for preparing a 3-alkenylcephem compound of formula (2), the process being characterized by adding at least one of organic solvents selected from the group consisting of alcohols, ethers, aliphatic hydrocarbons, alicyclic ketones and aliphatic ketones to a first solution of a 3-alkenylcephem compound of formula (1) in water or in a solvent mixture of water and at least one organic solvent selected from the group consisting of alcohols, aliphatic ketones, esters, amides and nitriles for crystallization to obtain a second solution or suspension of a 3-alkenylcephem compound of the formula (1), and adjusting the second solution or suspension to a pH of 0.5 to 4

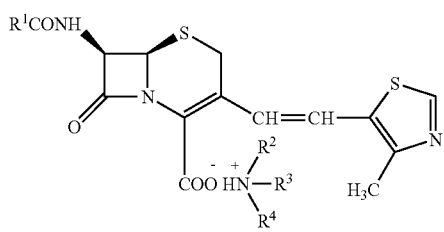
(1)

wherein $R^1$ is benzyl or phenoxymethyl, $R^2$, $R^3$ and $R^4$ are the same or different and are each a hydrogen atom, $C_{1-10}$ alkyl, $C_{4-8}$ cycloalkyl, or $C_{1-3}$ alkyl substituted with aryl where the aryl is optionally substituted with $C_{1-4}$ alkyl, or $R^2$ and $R^3$, when taken together, form a group —$(CH_2)_l X_m (CH_2)_n$— optionally substituted with $C_{1-4}$ alkyl, X is an oxygen atom or group —$N(R^5)$—, l is 0 to 3, m is 0 or 1, n is an integer of 2 to 4, and $R^5$ is a hydrogen atom or $C_{1-4}$ alkyl,

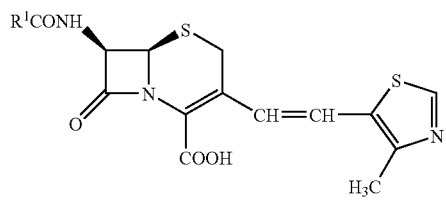
(2)

wherein $R^1$ is the same as in formula (1)

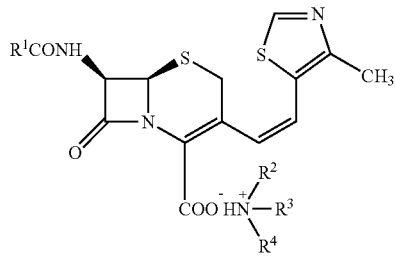
(1a)

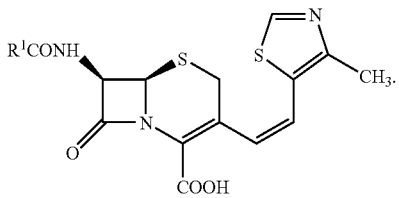
(2a)

2. A process for preparing 3-alkenylcephem compound of formula (1) which is improved in the content of a 3-(Z)-alkenylcephem compound of formula (1a) relative to a starting 3-alkenylcephem compound of formula (1), the process being characterized by adding at least one of organic solvents selected from the group consisting of alcohols, ethers, aliphatic hydrocarbons, alicyclic ketones and aliphatic ketones to a solution of the starting 3-alkenylcephem compound of the formula (1) in water or in a solvent mixture of water and at least one organic solvent selected from the group consisting of alcohols, aliphatic ketones, esters, amides and nitriles to crystallize the 3-alkenylcephem compound of the formula (1)

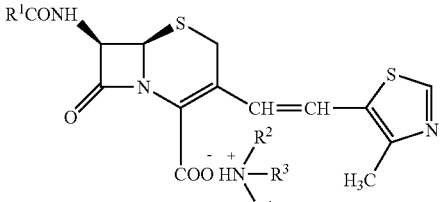
(1)

wherein R¹ is benzyl or phenoxymethyl, R², R³ and R⁴ are the same or different and are each a hydrogen atom, $C_{1-10}$ alkyl, $C_{4-9}$ cycloalkyl or $C_{1-3}$ alkyl substituted with aryl where the aryl is optionally substituted with $C_{1-4}$ alkyl, or R² and R³, when taken together, form a group —$(CH_2)_l X_m (CH_2)_n$— optionally substituted with $C_{1-4}$ alkyl, X is an oxygen atom or group —$N(R^5)$—, l is 0 to 3, m is 0 or 1, n is an integer of 2 to 4, and R⁵ is a hydrogen atom or $C_{1-4}$ alkyl,

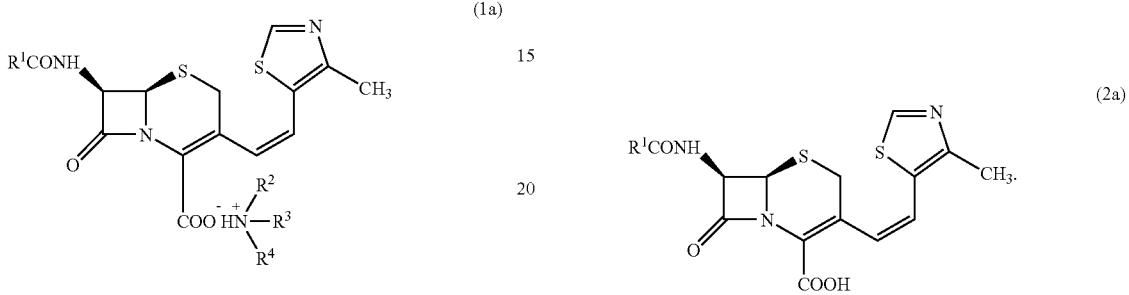

(1a)

wherein R¹, R², R³ and R⁴ are as defined in formula (1).

3. A process for preparing a 3-alkenylcephem compound of formula (2), the process being characterized by adjusting a solution or suspension of a 3-alkenylcephem compound of formula (1) to a pH of 0.5 to 4

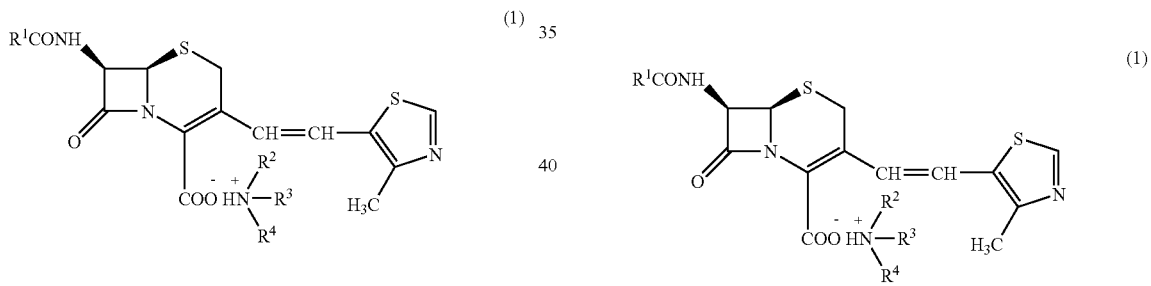

(1)

wherein R¹ is benzyl or phenoxymethyl, R², R³ and R⁴ are the same or different and are each a hydrogen atom, $C_{1-10}$ alkyl, $C_{4-8}$ cycloalkyl or $C_{1-3}$ alkyl substituted with aryl where the aryl is optionally substituted with $C_{1-4}$ alkyl, or R² and R³, when taken together, form a group —$(CH_2)_l X_m (CH_2)_n$— optionally substituted with $C_{1-4}$ alkyl, X is an oxygen atom or group —$N(R^5)$—, l is 0 to 3, m is 0 or 1, n is an integer of 2 to 4, and R⁵ is a hydrogen atom or $C_{1-4}$ alkyl,

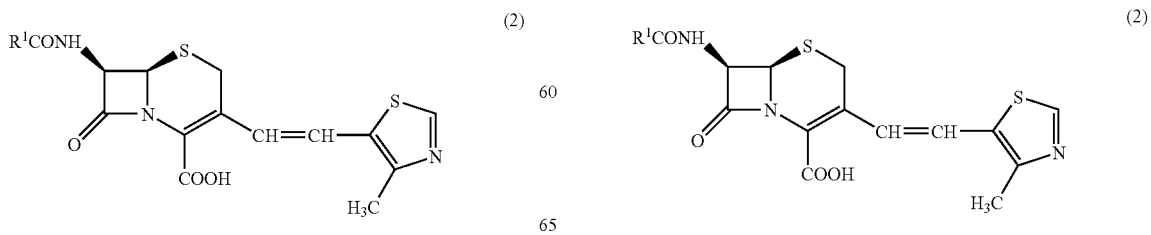

(2)

wherein R¹ is the same as in formula (1)

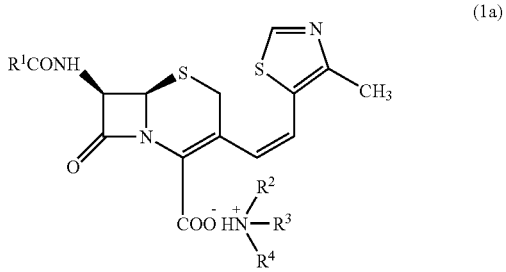

(1a)

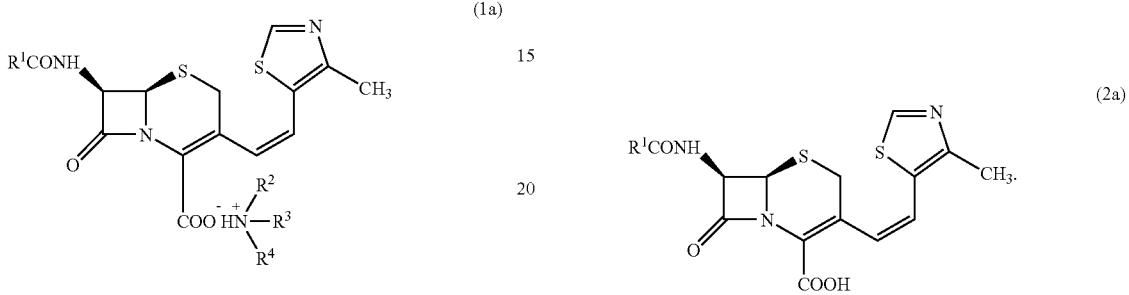

(2a)

4. A process for preparing a 3-alkenylcephem compound of formula (1) characterized by reacting an amine compound of formula (3) with a 3-alkenylcephem compound of formula (2) containing 1 to 15% of a 3-(E)-alkenylcephem compound of formula (2b)

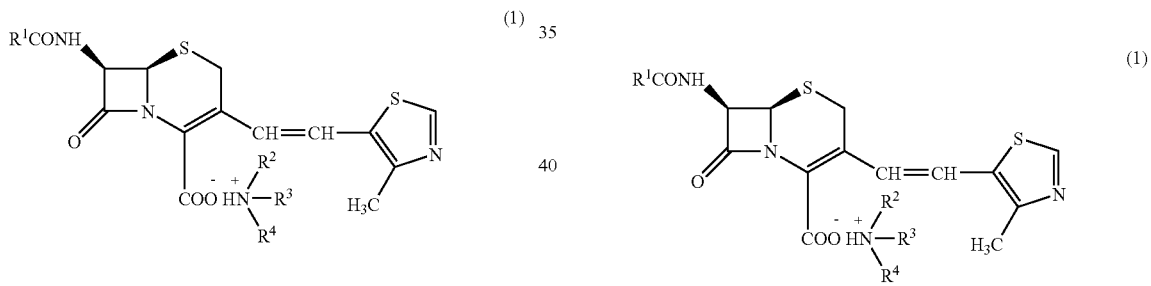

(1)

wherein R¹ is benzyl or phenoxymethyl, R², R³ and R⁴ are the same or different and are each a hydrogen atom, $C_{1-10}$ alkyl, $C_{4-9}$ cycloalkyl, or $C_{1-3}$ alkyl substituted with aryl where the aryl is optionally substituted with $C_{1-4}$ alkyl, or R² and R³, when taken together, form a group —$(CH_2)_l X_m (CH_2)_n$— optionally substituted with $C_{1-4}$ alkyl, X is an oxygen atom or group —$N(R^5)$—, l is 0 to 3, m is 0 or 1, n is an integer of 2 to 4, and R⁵ is a hydrogen atom or $C_{1-4}$ alkyl,

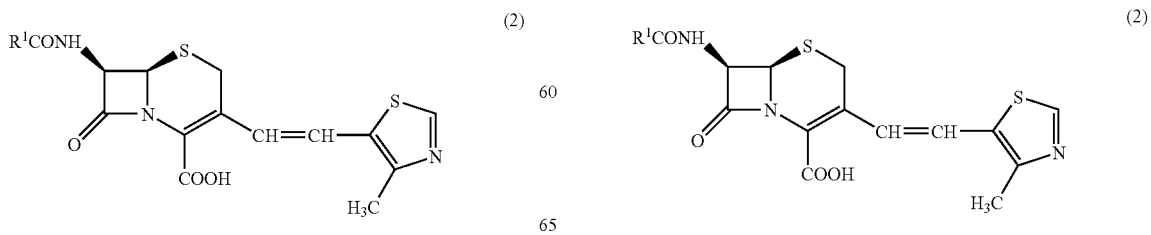

(2)

wherein R¹ is the same as in formula (1),

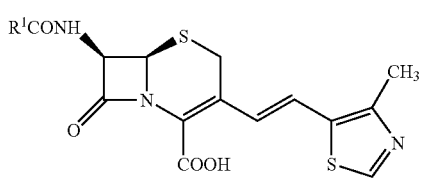

wherein $R^2$, $R^3$ and $R^4$ are the same as in formula (1),

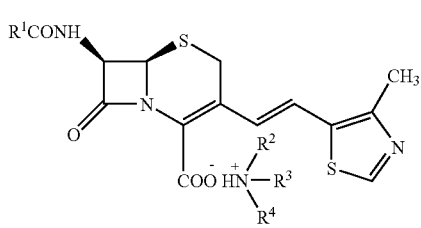

wherein $R^1$ is the same as in formula (1).

5. A process according to claim 2 for preparing the 3-alkenylcephem compound of the formula (1) which is improved in the content of a 3-(Z)-alkenylcephem compound of the formula (1a) relative to the starting 3-alkenylcephem compound of formula (1), the process being characterized by adding at least one of organic solvents selected from the group consisting of alcohols, ethers, aliphatic hydrocarbons, alicyclic ketones and aliphatic ketones to a solution of the starting 3-alkenylcephem compound of the formula (1) containing 1 to 15% of a 3-(E)-alkenylcephem compound of formula (1b) in water or in a solvent mixture of water and at least one organic solvent selected from the group consisting of alcohols, aliphatic ketones, esters, amides and nitriles to crystallize the 3-alkenylcephem compound of the formula (1)

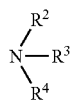

wherein $R^1$, $R^2$, $R^3$ and $R^4$ are the same as in formula (1).

6. A process according to claim 2 for preparing the 3-alkenylcephem compound of the formula (1) which is improved in the content of a 3-(Z)-alkenylcephem compound of the formula (1a) relative to the starting 3-alkenylcephem compound of formula (1), the process being characterized by adding 3 to 30 parts by volume of at least one of organic solvents selected from the group consisting of alcohols, ethers, aliphatic hydrocarbons, alicyclic ketones and aliphatic ketones to a solution of 1 part by weight of the starting 3-alkenylcephem compound of the formula (1) in 2 to 50 parts by volume of water or a solvent mixture of water and at least one organic solvent selected from the group consisting of alcohols, aliphatic ketones, esters, amides and nitriles for crystallization.

7. A process according to claim 2 for preparing 3-alkenylcephem compound of the formula (1) improved in the content of a 3-(Z)-alkenylcephem compound of the formula (1a) relative to the starting 3-alkenylcephem compound of formula (1), wherein the solvent mixture of water and organic solvent is an acetone/water solvent mixture or methanol/water solvent mixture.

8. A process according to claim 2 for preparing a 3-alkenylcephem compound of the formula (1) improved in the content of a 3-(Z)-alkenylcephem compound of the formula (1a) relative to the starting 3-alkenylcephem compound of formula (1), wherein the solvent mixture of water and organic solvent has a mixing ratio of 1 to 10 parts by volume of the organic solvent per part by volume of water.

9. A process according to claim 2 for preparing a 3-alkenylcephem compound of the formula (1) improved in the content of a 3-(Z)-alkenylcephem compound of the formula (1a) relative to the starting 3-alkenylcephem compound of formula (1), wherein the organic solvent to be added to the solution of the starting 3-alkenylcephem compound of the formula (1) is methanol, diethyl ether, diisopropyl ether, acetone, n-hexane or n-hexanone.

10. A process according to claim 2 for preparing a 3-alkenylcephem compound of the formula (1) improved in the content of a 3-(Z)-alkenylcephem compound of the formula (1a) relative to the starting 3-alkenylcephem compound of formula (1), wherein the content of the 3-(Z)-alkenylcephem compound of the formula (1a) in the 3-alkenylcephem compound of the formula (1) improved in the content of a 3-(Z)-alkenylcephem compound of the formula (1a) is at least 96%.

11. A process for preparing a 3-(Z)-alkenylcephem compound of the formula (2a) according to claim 3, the process being characterized by dissolving or suspending a 3-(Z)-alkenylcephem compound of the formula (1a) in water and adjusting the resulting solution or suspension to a pH of 0.5 to 4 with a mineral acid.

12. A process for preparing a 3-alkenylcephem compound of the formula (2), the process being characterized by dissolving or suspending a 3-alkenylcephem compound of the formula (1) in water and adjusting the resulting solution or suspension to a pH of 0.5 to 4 with a mineral acid

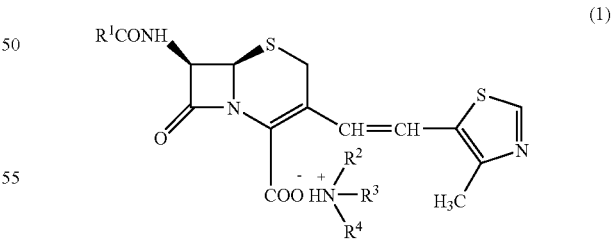

wherein $R^1$ is benzyl or phenoxymethyl, $R^2$, $R^3$ and $R^4$ are the same or different and are each a hydrogen atom, $C_{1-10}$ alkyl, $C_{4-8}$ cycloalkyl, or $C_{1-3}$ alkyl substituted with aryl where the aryl is optionally substituted with $C_{1-4}$ alkyl, or $R^2$ and $R^3$, when taken together, form a group $-(CH_2)_l X_m (CH_2)_n-$ optionally substituted with alkyl, X is an oxygen atom or group $-N(R^5)-$, l is 0 to 3, m is 0 or 1, n is an integer of 2 to 4, and $R^5$ is a hydrogen atom or $C_{1-4}$ alkyl,

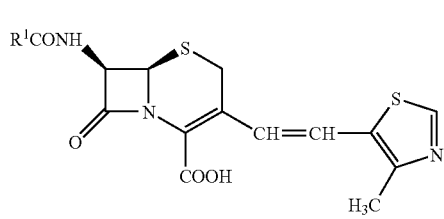
(2)
wherein R¹ is the same as in formula (1)
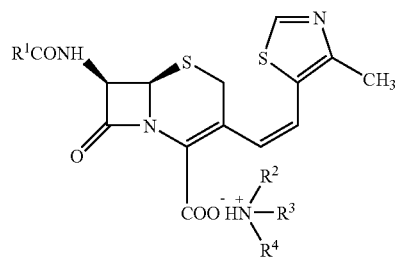
(1a)
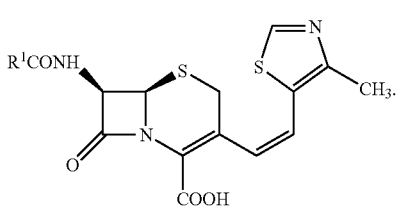
(2a)
13. A process according to claim 3 for preparing the 3-alkenylcephem compound of the formula (2), wherein the content of a 3-(Z)-alkenylcephem compound of the formula (2a) in the 3-alkenylcephem compound of the formula (2) is at least 96%.
* * * * *